United States Patent
Lemaitre

(10) Patent No.: US 10,121,629 B2
(45) Date of Patent: Nov. 6, 2018

(54) ANGLED FLAT EMITTER FOR HIGH POWER CATHODE WITH ELECTROSTATIC EMISSION CONTROL

(71) Applicant: GENERAL ELECTRIC COMPANY, Schenectady, NY (US)

(72) Inventor: Sergio Lemaitre, Milwaukee, WI (US)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 15/820,955

(22) Filed: Nov. 22, 2017

(65) Prior Publication Data

US 2018/0096816 A1    Apr. 5, 2018

Related U.S. Application Data

(63) Continuation-in-part of application No. 15/086,257, filed on Mar. 31, 2016.

(60) Provisional application No. 62/425,903, filed on Nov. 23, 2016.

(51) Int. Cl.
| | |
|---|---|
| *H01J 35/06* | (2006.01) |
| *H01J 35/14* | (2006.01) |
| *H01J 35/08* | (2006.01) |
| *A61B 6/03* | (2006.01) |
| *H01J 35/04* | (2006.01) |

(52) U.S. Cl.
CPC ............. *H01J 35/14* (2013.01); *A61B 6/032* (2013.01); *H01J 35/045* (2013.01); *H01J 35/06* (2013.01); *H01J 35/065* (2013.01); *H01J 35/08* (2013.01)

(58) Field of Classification Search
CPC .... H01J 35/045; H01J 35/06; H01J 2235/068; H01J 2235/06; H01J 35/14
See application file for complete search history.

(56) References Cited

U.S. PATENT DOCUMENTS

| | | | |
|---|---|---|---|
| 2012/0321048 A1* | 12/2012 | Hubbard | H01J 35/06 378/136 |
| 2016/0217965 A1* | 7/2016 | Canfield | H01J 35/045 |
| 2017/0372864 A1* | 12/2017 | Anno | H01J 35/14 |

* cited by examiner

*Primary Examiner* — Don Wong
(74) *Attorney, Agent, or Firm* — Global Patent Operation; Marc A. Vivenzio

(57) ABSTRACT

In the present invention, a computed tomography system, an X-ray tube used therein and a cathode assembly disposed in the X-ray tube, as well as an associated method of use, is provided that includes a gantry and the X-ray tube coupled to the gantry. The X-ray tube includes the cathode assembly having a pair of emission surfaces for generating an electron beam, where the pair of emission surfaces are disposed in the cathode assembly at angles with respect to one another. The X-ray tube further includes a focusing electrode for focusing the electron beam, an extraction electrode which electrostatically controls the intensity of the electron beam by adjustment of a positive or negative biasing voltage applied to the extraction electrode, a target for generating X-rays when impinged upon by the electron beam and a magnetic focusing assembly located between the cathode assembly and the target for focusing the electron beam towards the target.

22 Claims, 14 Drawing Sheets

ANGLED FLAT EMITTER FOR HIGH POWER CATHODE WITH ELECTROSTATIC EMISSION CONTROL

BACKGROUND

Embodiments of the invention relate generally to X-ray tubes and more particularly to an apparatus for improved focusing control and increased useful life of the tube.

Typically, in computed tomography (CT) imaging systems, an X-ray source emits a fan-shaped beam or a cone-shaped beam towards a subject or an object, such as a patient or a piece of luggage. Hereinafter, the terms "subject" and "object" may be used to include anything that is capable of being imaged. The beam, after being attenuated by the subject, impinges upon an array of radiation detectors. The intensity of the attenuated beam radiation received at the detector array is typically dependent upon the attenuation of the X-ray beam by the subject. Each detector element of a detector array produces a separate electrical signal indicative of the attenuated beam received by each detector element. The electrical signals are transmitted to a data processing system for analysis. The data processing system processes the electrical signals to facilitate generation of an image.

Generally, in CT systems the X-ray source and the detector array are rotated about a gantry within an imaging plane and around the subject. Furthermore, the X-ray source generally includes an X-ray tube, which emits the X-ray beam at a focal point. Also, the X-ray detector or detector array typically includes a collimator for collimating X-ray beams received at the detector, a scintillator disposed adjacent to the collimator for converting X-rays to light energy, and photodiodes for receiving the light energy from the adjacent scintillator and producing electrical signals therefrom.

Currently available X-ray tubes employed in CT systems fail to control the level of electron beam intensity to a desired temporal resolution. Several attempts have been made in this area by employing techniques such as controlling the heating of the filament, employing Wehnelt Cylinder gridding that is typically used in vascular X-ray sources and by employing an electron acceleration hood on the target of the X-ray tube to control electron beam intensity. Also, currently available microwave sources include an electron gun that includes a focusing electrode, such as a Pierce electrode to generate an electron beam. These electron guns typically include a grid to control a beam current magnitude via use of control grid means. Unfortunately, the energy and duty cycle of the electron beam makes the introduction of an intercepting wire mesh grid difficult since the thermo-mechanical stresses in the grid wires are reduced when the intercepted area of the electron beam is minimized. Furthermore, rapidly changing the electron beam current prevents proper positioning and focusing of the electron beam on the X-ray target. Modulation of the electron beam current from 0 percent to 100 percent of the electron beam intensity changes the forces in the electron beam, due to changes in the space charge force resulting in change in the desired electro-magnetic focusing and deflection.

In addition, current X-ray tubes have limitations with regard to the emission current that can be utilized in the X-ray tube. The primary reason for this is that higher emission currents cause the emitter in the X-ray tube to fail prematurely as a result of the increased temperature leading to accelerated burnout of the emitter at these emission current levels.

Hence, it is desirable to control focus and position of the electron beam on a same time scale to preserve image quality, imaging system performance, and durability of the X-ray source. It is also desirable to increase the emission current capable of being utilized in the X-ray source/X-ray tube without compromising the useful life of the X-ray tube.

BRIEF DESCRIPTION

There is a need or desire for a system and method to emit an electron beam from an X-ray tube using higher emission currents without degrading the useful life of the X-ray tube. The above-mentioned drawbacks and needs are addressed by the embodiments described herein in the following description.

According to one aspect of one exemplary embodiment of the invention, an X-ray tube includes a cathode assembly on which is disposed a pair of emission surfaces for generating a pair of electron beams, the pair of emission surfaces disposed at an angle with regard to one another.

Briefly in accordance with one exemplary aspect of the invention, an injector or cathode assembly for an X-ray tube is presented. The injector includes a pair of emission surfaces that may be flat, curved, partially curved or any combination thereof that each emit streams of electrons from an that can combine to form an electron beam, at least one focusing electrode disposed around the emission surfaces, wherein the at least one focusing electrode focuses the electron beam and at least one extraction electrode that can be adjusted between a positive and negative bias with respect to the emission surfaces, wherein the at least one extraction electrode controls an intensity of the electron beam. The pair of emission surfaces can be formed as a pair of emitters that may be flat, curved, partially curved or any combination thereof and that provide a large emission surface/emitter area that can accommodate large emission currents with an extended emitter lifespan. The angled position of the emission surfaces/emitters in the cathode assembly or injector enables the electron beams emitted by each emission surface/emitter to provide an initial convergence of the beams to overcome the space charge of the electrons in the respective beams. This, in turn enables the waist of the converging electron beams to be positioned at a location in front of a magnetic focusing assembly at large and small emission currents, thereby enabling the magnetic focusing assembly to effectively affect/focus and direct the electron beam onto the desired focal spot. Further, by maintaining the position of the beam waist upstream or in front of the magnetic focusing assembly, the energy or current needed to be supplied to the magnetic focusing assembly to focus the electron beam is within normal ranges.

In accordance with another exemplary aspect of the invention, an X-ray tube is presented. The X-ray tube includes an injector including a pair of emitters to emit an electron beam singly or in combination with one another, at least one focusing electrode disposed around the emitter, wherein the at least one focusing electrode focuses the electron beam and at least one extraction electrode for controlling an intensity of the electron beam, wherein the at least one extraction electrode can be adjusted between a positive and negative bias voltage with respect to the emitters. Further, the X-ray tube also includes a target for generating X-rays when impinged upon by the electron beam and a magnetic assembly located between the injector and the target for directionally influencing focusing, deflecting and/or positioning the electron beam towards the target.

In accordance with a further exemplary aspect of the invention, a computed tomography system is presented. The computed tomography system includes a gantry and an X-ray tube coupled to the gantry. The X-ray tube includes a tube casing and an injector including a pair of emitters to emit an electron beam, at least one focusing electrode disposed around the emitters, wherein the at least one focusing electrode focuses the electron beam and at least one extraction electrode for controlling an intensity of the electron beam, wherein the at least one extraction electrode can be adjusted between a positive and negative bias with respect to the emitters. The X-ray tube also includes a target for generating X-rays when impinged upon by the electron beam and a magnetic assembly located between the injector and the target for directionally influencing focusing deflecting and/or positioning the electron beam towards the target. Further, the computed tomography system includes an X-ray controller for providing power and timing signals to the X-ray tube and one or more detector elements for detecting attenuated X-ray beam from an imaging object.

According to another aspect of one exemplary embodiment of the invention, X-ray tube including a cathode assembly on which is disposed a pair of emission surfaces for generating a pair of electron beams, the pair of emission surfaces disposed at an angle with regard to one another, a focusing electrode adjacent the cathode assembly for focusing the electron beams, an extraction electrode spaced from the focusing electrode opposite the cathode assembly for controlling the intensity of the electron beam by adjusting a positive or negative voltage applied to the extraction electrode, a magnetic assembly spaced from the extraction electrode opposite the focusing electrode and a target spaced from the magnetic assembly opposite the extraction electrode.

According to still another aspect of one exemplary embodiment of the invention, a cathode assembly includes an emitter having a first emission surface configured to emit a first electron beam therefrom and a second emission surface disposed on the cathode assembly and configured to emit a second electron beam therefrom, wherein the first emission surface and the second emission surface are disposed at an angle with regard to one another.

According to still a further aspect of one exemplary embodiment of the invention, a method for focusing an electron beam emitted from an X-ray tube includes the steps of providing an X-ray tube including a cathode assembly on which is disposed a pair of emission surfaces for generating a pair of electron beams, the pair of emission surfaces disposed at an angle with regard to one another, a focusing electrode adjacent the cathode assembly, an extraction electrode spaced from the focusing electrode opposite the cathode assembly that can be can be adjusted between a positive and negative bias relative to the pair of emission surfaces, a magnetic assembly spaced from the extraction electrode opposite the focusing electrode and a target spaced from the magnetic assembly opposite the extraction electrode capable of generating X-rays when impinged upon by the electron beams, passing an emission current through at least one of the pair of emission surfaces to generate an electron beam; and passing a focusing current through the magnetic assembly to focus the electron beam onto the target.

According to still a further aspect of one exemplary embodiment of the invention, a computed tomography system includes a gantry, an X-ray tube coupled to the gantry, the X-ray tube including a cathode assembly having a pair of emission surfaces for generating an electron beam, the pair of emission surfaces disposed therein at angles with respect to one another, a focusing electrode for focusing the electron beam; an extraction electrode which controls the intensity of the electron beam though the adjustment of a positive or negative biasing voltage applied to the extraction electrode; a target for generating X-rays when impinged upon by the electron beam, a magnetic assembly located between the cathode assembly and the target for focusing the electron beam towards the target, an X-ray controller for providing power and timing signals to the X-ray tube and one or more detector elements for detecting attenuated X-ray beam from an imaging object.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The drawings illustrate the best mode presently contemplated of carrying out the disclosure. In the drawings.

DETAILED DESCRIPTION

In the following detailed description, reference is made to the accompanying drawings that form a part hereof, and in which is shown by way of illustration specific embodiments, which may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken in a limiting sense.

Exemplary embodiments of the invention relate to an X-ray tube including an increased emitter area to accommodate larger emission currents in conjunction with microsecond X-ray intensity switching in the X-ray tube. An exemplary X-ray tube and a computed tomography system employing the exemplary X-ray tube are presented.

Figure 1:
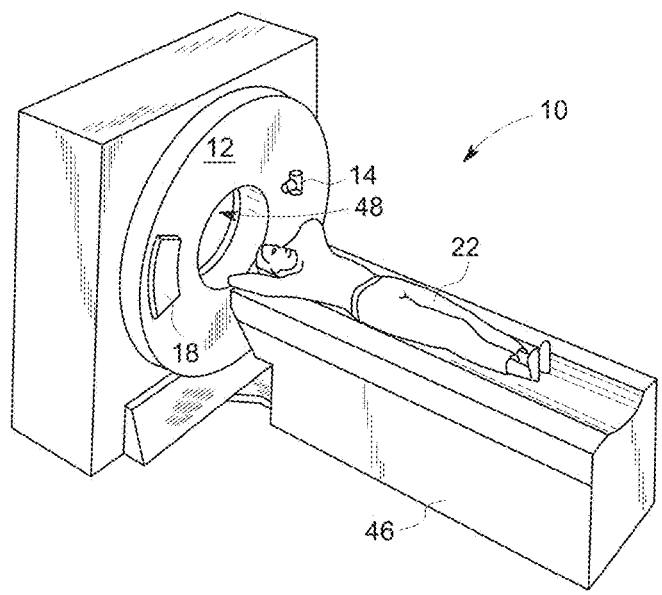
FIG. 1 is a schematic representation of a CT imaging system according to an exemplary embodiment of the invention.
Figure 2:
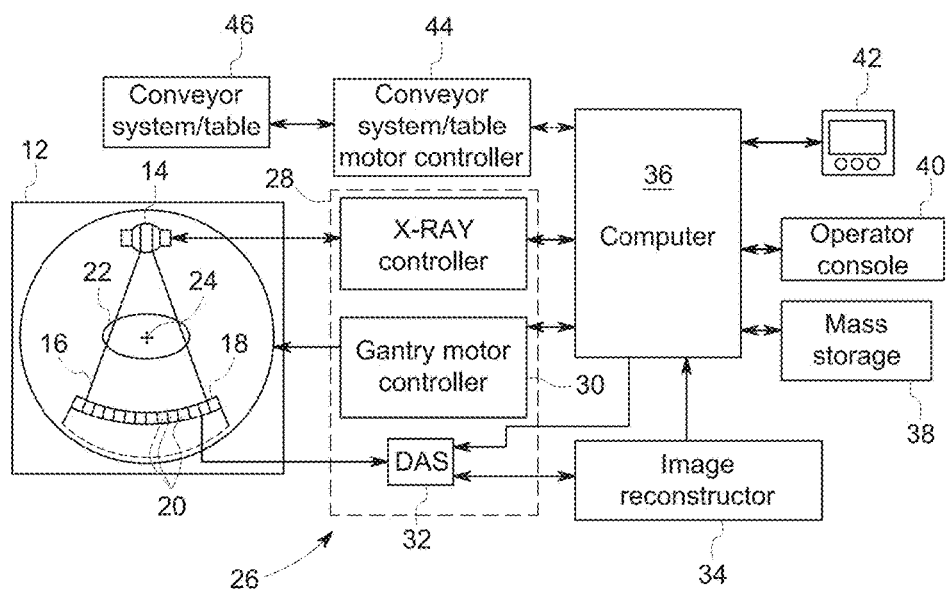
FIG. 2 is a block schematic diagram of the CT imaging system illustrated in FIG. 1.

Referring now to FIGS. 1 and 2, a computed tomography (CT) imaging system 10 is illustrated in accordance with one exemplary embodiment of the invention, such as that disclosed in co-owned U.S. Pat. No. 8,401,151, entitled "X-Ray Tube For Microsecond X-Ray Intensity Switching", the entirety of which is expressly incorporated by reference herein for all purposes. The CT imaging system 10 includes a gantry 12. The gantry 12 has an X-ray source 14, which typically is an X-ray tube that projects a beam of X-rays 16 towards a detector array 18 positioned opposite the X-ray tube on the gantry 12. In one embodiment, the gantry 12 may have multiple X-ray sources (along the patient theta or patient Z axis) that project beams of X-rays. The detector array 18 is formed by a plurality of detectors 20 which together sense the projected X-rays that pass through an object to be imaged, such as a patient 22. During a scan to acquire X-ray projection data, the gantry 12 and the components mounted thereon rotate about a center of rotation 24. While the CT imaging system 10 described with reference to the medical patient 22, it should be appreciated that the CT imaging system 10 may have applications outside the medical realm. For example, the CT imaging system 10 may be utilized for ascertaining the contents of closed articles, such as luggage, packages, etc., and in search of contraband such as explosives and/or biohazardous materials.

Rotation of the gantry 12 and the operation of the X-ray source 14 are governed by a control mechanism 26 of the CT system 10. The control mechanism 26 includes an X-ray controller 28 that provides power and timing signals to the X-ray source 14 and a gantry motor controller 30 that controls the rotational speed and position of the gantry 12. A data acquisition system (DAS) 32 in the control mechanism 26 samples analog data from the detectors 20 and converts the data to digital signals for subsequent processing. An image reconstructor 34 receives sampled and digitized X-ray data from the DAS 32 and performs high-speed reconstruction. The reconstructed image is applied as an input to a computer 36, which stores the image in a mass storage device 38.

Moreover, the computer 36 also receives commands and scanning parameters from an operator via operator console 40 that may have an input device such as a keyboard (not shown in FIGS. 1-2). An associated display 42 allows the operator to observe the reconstructed image and other data from the computer 36. Commands and parameters supplied by the operator are used by the computer 36 to provide control and signal information to the DAS 32, the X-ray controller 28 and the gantry motor controller 30. In addition, the computer 36 operates a table motor controller 44, which controls a motorized table 46 to position the patient 22 and the gantry 12. Particularly, the table 46 moves portions of patient 22 through a gantry opening 48. It may be noted that in certain embodiments, the computer 36 may operate a conveyor system controller 44, which controls a conveyor system 46 to position an object, such as, baggage or luggage and the gantry 12. More particularly, the conveyor system 46 moves the object through the gantry opening 48.

The X-ray source 14 is typically an X-ray tube that includes at least a cathode and an anode. The cathode may be a directly heated cathode or an indirectly heated cathode. Currently, X-ray tubes include an electron source to generate an electron beam and impinge the electron beam on the anode to produce X-rays. These electron sources control a beam current magnitude by changing the current on the filament, and therefore emission temperature of the filament. Unfortunately, these X-ray tubes fail to control electron beam intensity to a view-to-view basis based on scanning requirements, thereby limiting the system imaging options. Accordingly, an exemplary X-ray tube is presented, where the X-ray tube provides microsecond current control during nominal operation, on/off gridding for gating or usage of multiple X-ray sources, 0 percent to 100 percent modulation for improved X-ray images, and dose control or fast voltage switching for generating X-rays of desired intensity resulting in enhanced image quality.

Figure 3:
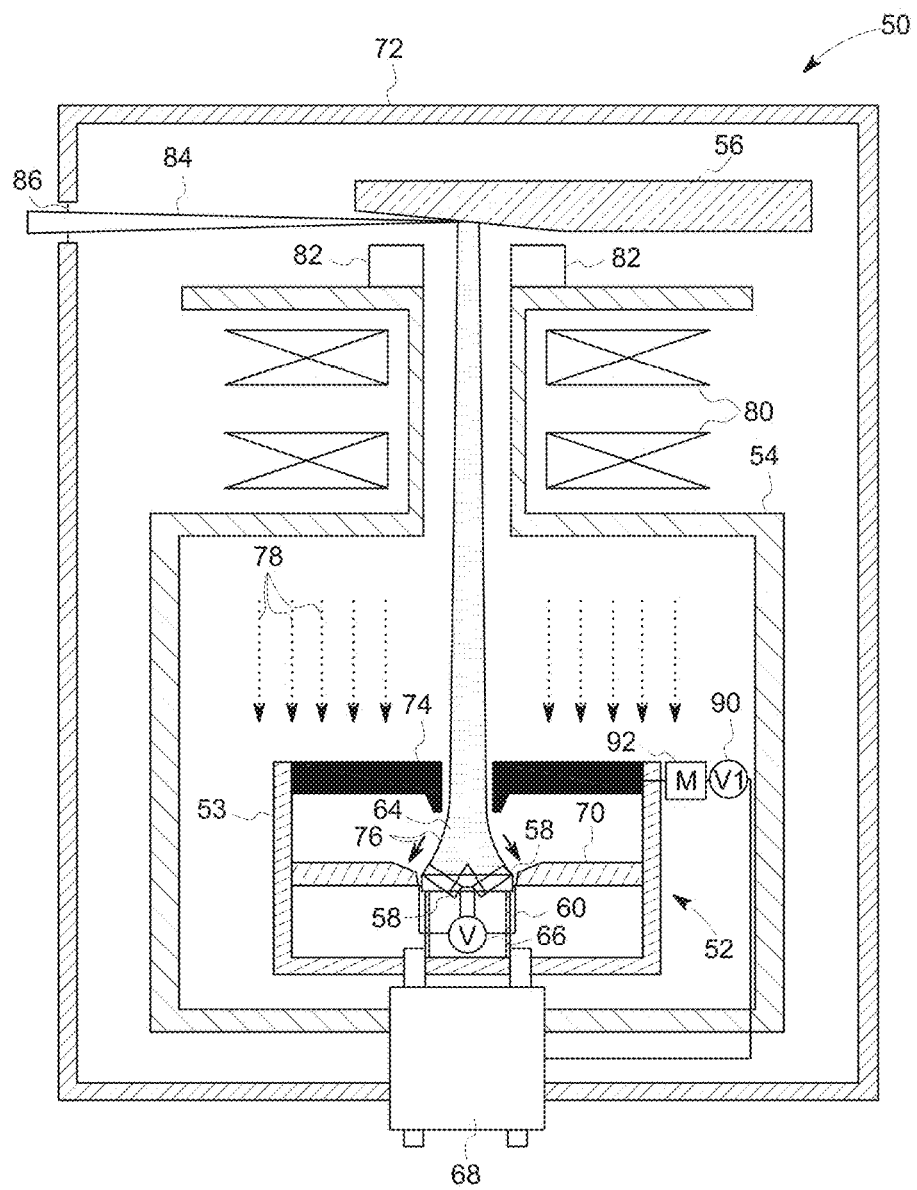
FIG. 3 is a schematic representation of an X-ray tube according to still another exemplary embodiment of the invention.

FIG. 3 is a diagrammatical illustration of an exemplary X-ray tube 50, in accordance with aspects of the present technique. In one embodiment, the X-ray tube 50 may be the X-ray source 14 (see FIGS. 1-2). In the illustrated embodiment, the X-ray tube 50 includes an exemplary injector or cathode assembly 52 disposed within a vacuum wall 54. Further, the injector 52 includes an injector wall 53 that encloses various components of the injector 52. In addition, the X-ray tube 50 also includes an anode 56. The anode 56 is typically an X-ray target. The injector 52 and the anode 56 are disposed within a tube casing 72. In accordance with aspects of the present technique, the injector 52 may include at least one cathode in the form of a pair of emitters 58. In the present example, the cathode, and in particular the emitters 58, may be directly heated. Further, the emitters 58 may be coupled to an emitter support/cathode cup 60, and the emitter support/cathode cup 60 in turn may be coupled to the injector wall 53. The emitters 58 may be heated by passing a large current through the emitters 58. A voltage source 66 may supply this current to the emitters 58. In one embodiment, a current of about 10 amps (A) may be passed through the emitters 58. The emitters 58 may emit an electron beam 64 as a result of being heated by the current supplied by the voltage source 66. As used herein, the term "electron beam" may be used to refer to a stream of electrons that have substantially similar velocities.

The electron beam 64 may be directed towards the target 56 to produce X-rays 84. More particularly, the electron beam 64 may be accelerated from the emitters 58 towards the target 56 by applying a potential difference between the emitters 58 and the target 56. In one embodiment, a high voltage in a range from about 40 kV to about 450 kV may be applied via use of a high voltage feedthrough 68 to set up a potential difference between the emitters 58 and the target 56, thereby generating a high voltage main electric field 78. In one embodiment, a high voltage differential of about 140 kV may be applied between the emitters 58 and the target 56 to accelerate the electrons in the electron beam 64 towards the target 56. It may be noted that in the presently contemplated configuration, the target 56 may be at ground potential. By way of example, the emitters 58 may be at a potential of about −140 kV and the target 56 may be at ground potential or about zero volts.

In an alternative embodiment, emitters 58 may be maintained at ground potential and the target 56 may be maintained at a positive potential with respect to the emitters 58. By way of example, the target may be at a potential of about 140 kV and the emitters 58 may be at ground potential or about zero volts. In still another alternative embodiment, the emitters 58 can have a potential of −70 kV while the target 56 has a potential of +70 kV.

Moreover, when the electron beam 64 impinges upon the target 56, a large amount of heat is generated in the target 56. Unfortunately, the heat generated in the target 56 may be significant enough to melt the target 56. In accordance with aspects of the present technique, a rotating target may be used to circumvent the problem of heat generation in the target 56. More particularly, in one embodiment, the target 56 may be configured to rotate such that the electron beam 64 striking the target 56 does not cause the target 56 to melt since the electron beam 64 does not strike the target 56 at the same location. In another embodiment, the target 56 may include a stationary target. Furthermore, the target 56 may be made of a material that is capable of withstanding the heat generated by the impact of the electron beam 64. For example, the target 56 may include materials such as, but not limited to, tungsten, molybdenum, or copper.

Figure 17:
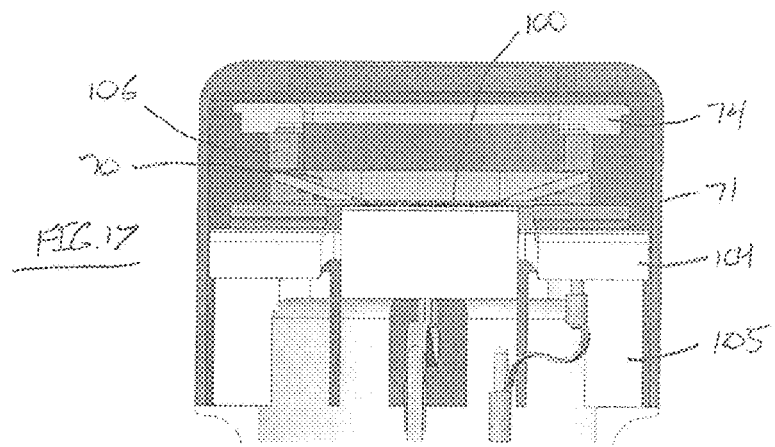
FIG. 17 is a cross-sectional view of a cathode assembly according to another exemplary embodiment of the invention.
Figure 16:
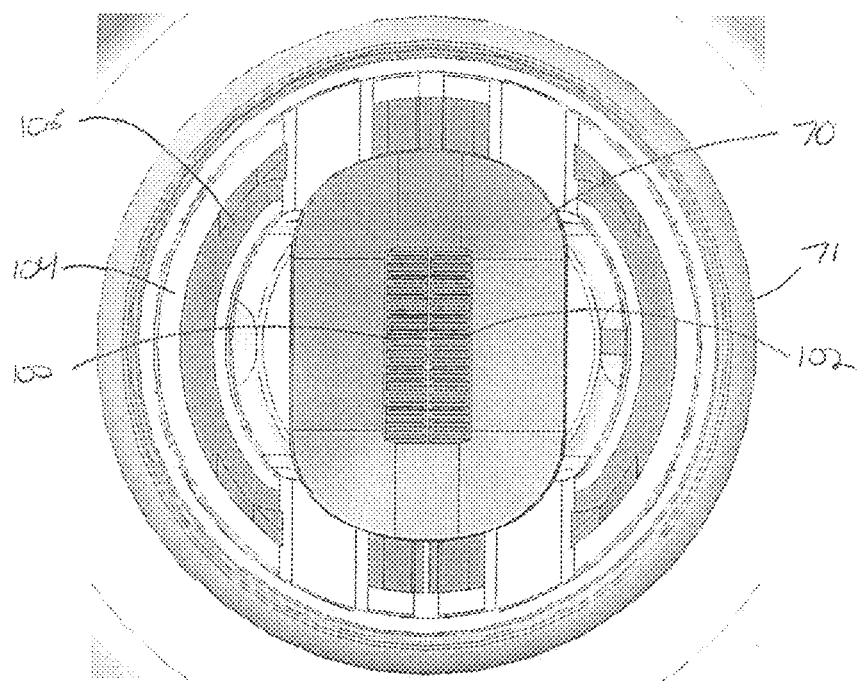
FIG. 16 is a top plan view of a cathode assembly according to one exemplary embodiment of the invention.

With continuing reference to FIGS. 3, 16 and 17 the injector/cathode assembly 52 may include at least one focusing electrode 70 within a shield 71. In one embodiment, the at least one focusing electrode 70 may be disposed adjacent to the emitters 58 such that the focusing electrode 70 focuses the electron beam 64 towards the target 56. As used herein, the term "adjacent" means near to in space or position. Further, in one embodiment, the focusing electrode 70 may be maintained at a voltage potential that is less than a voltage potential of the emitters 58. The potential difference between the emitters 58 and focusing electrode 70 prevents electrons generated from the emitters 58 from moving towards the focusing electrode 70. In one embodiment, the focusing electrode 70 may be maintained at a negative potential with respect to that of the emitters 58. The negative potential of the focusing electrode 70 with respect to the emitters 58 focuses the electron beam 64 away from the focusing electrode 70 and thereby facilitates focusing of the electron beam 64 towards the target 56.

In another embodiment, the focusing electrode 70 may be maintained at a voltage potential that is equal to or substantially similar to the voltage potential of the emitter 58. The similar voltage potential of the focusing electrode 70 with respect to the voltage potential of the emitters 58 creates a parallel electron beam by shaping electrostatic fields due to the shape of the focusing electrode 70. The focusing electrode 70 may be maintained at a voltage potential that is equal to or substantially similar to the voltage potential of the emitters 58 via use of a lead (not shown in FIG. 3) that couples the emitters 58 and the focusing electrode 70.

Moreover, in accordance with aspects of the present technique, the injector 52 includes at least one extraction electrode 74 positioned on and electrically insulated from the emitters 58 and the focusing electrode 70 by a support/insulation 106 (FIG. 7) for additionally controlling and focusing the electron beam 64 towards the target 56. In one embodiment, the at least one extraction electrode 74 is located between the target 56 and the emitters 58. Furthermore, in certain embodiments, the extraction electrode 74 may be positively biased via use of a voltage tab (not shown in FIG. 3) for supplying a desired voltage to the extraction electrode 74. In accordance with aspects of the present technique, a bias voltage power supply 90 may supply a voltage to the extraction electrode 74 such that the extraction electrode 74 is maintained at a positive bias voltage with respect to the emitters 58. In one embodiment, the extraction electrode 74 may be divided into a plurality of regions having different voltage potentials to perform focusing or a biased emission from different regions of the emitters 58.

It may be noted that, in an X-ray tube, energy of an X-ray beam may be controlled via one or more of multiple ways. For instance, the energy of an X-ray beam may be controlled by altering the potential difference (that is acceleration voltage) between the cathode and the anode, or by changing the material of the X-ray target, or by filtering the electron beam. This is generally referred to as "kV control." As used herein, the term "electron beam current" refers to the flow of electrons per second between the cathode and the anode. Furthermore, an intensity of the X-ray beam is controllable via control of the electron beam current. Such a technique of controlling the intensity is generally referred to as "mA control." As discussed herein, aspects of the present technique provide for control of the electron beam current via use of the extraction electrode 74, or electrostatic mA control. It may be noted that, the use of such extraction electrode 74 enables a decoupling of the control of electron emission from the acceleration voltage.

Furthermore, the extraction electrode 74 is configured for microsecond current control. Specifically, the electron beam current may be controlled in the order of microseconds by altering the voltage applied to the extraction electrode 74 in the order of microseconds. It may be noted that the emitters 58 may be treated as an infinite source of electrons. In accordance with aspects of the present technique, electron beam current, which is typically a flow of electrons from the emitters 58 towards the target 56, may be controlled by altering the voltage potential of the extraction electrode 74. Control of the electron beam current will be described in greater detail hereinafter.

With continuing reference to FIG. 3, the extraction electrode 74 may also be biased at a positive voltage with respect to the focusing electrode 70. As an example, if the voltage potential of emitters 58 is about −140 kV, the voltage potential of the focusing electrode 70 may be maintained at about −140 kV or less, and the voltage potential of the extraction electrode 74 may be maintained at about −135 kV for positively biasing the extraction electrode 74 with respect to the emitters 58. In accordance with aspects of the present technique, an electric field 76 is generated between the extraction electrode 74 and the focusing electrode 70 due to a potential difference between the focusing electrode 70 and the extraction electrode 74. The strength of the electric field 76 thus generated may be employed to control the intensity of electron beam 64 generated by the emitters 58 towards the target 56. The intensity of the electron beam 64 striking the target 56 may thus be controlled by the electric field 76. More particularly, the electric field 76 causes the electrons emitted from the emitters 58 to be accelerated towards the target 56. The stronger the electric field 76, the stronger is the acceleration of the electrons from the emitters 58 towards the target 56. Alternatively, the weaker the electric field 76, the lesser is the acceleration of electrons from the emitters 58 towards the target 56.

In addition, altering the bias voltage on the extraction electrode 74 may modify the intensity of the electron beam 64. As previously noted, the bias voltage on the extraction electrode may be altered via use of the voltage tab present on the bias voltage power supply 90. Biasing the extraction electrode 74 more positively with respect to the emitter 58 results in increasing the intensity of the electron beam 64. Alternatively, biasing the extraction electrode 74 less positively or negatively with respect to the emitters 58 causes a decrease in the intensity of the electron beam 64.

The electron emission originating from the surface of a thermoionic electron emitter, the flat emitters, 100,102, strongly depends on the "pulling" electric field generated by the X-ray tube's anode 56. For enabling fast on/off switching of the tube 12, it is known from the relevant prior art that X-ray tubes of the rotary-anode type may be equipped with a grid electrode, e.g., the extraction electrode 74, placed in front of the electron emitters 100,102. To shut off the electron beam completely, a bias voltage is applied to the grid electrode which generates a repelling field and is usually given by the absolute value of the potential difference between the electron emitter and the grid electrode. The resulting electric field at the emitter surface is the sum of the grid and the anode generated field. If the total field is repelling on all locations on the electron emitter, electron emission is completely cut off.

In one embodiment, the electron beam 64 may be shut-off entirely by biasing the extraction electrode 74 negatively with respect to the emitters 58,100,102, as opposed to a positive bias on the extraction electrode 74 which serves to extract or accelerate the electron beam 64 away from the emitters 100,102. As previously noted, the positive or negative bias voltage on the extraction electrode 74 may be supplied via use of the bias voltage power supply 90. Hence, the intensity of the electron beam 64 may be controlled from 0 percent to 100 percent of possible intensity by changing the bias voltage on the extraction electrode 74 via use of the extractor voltage tab 91 present in the bias voltage power supply 90. The extraction electrode 74 controls emission from 0 mA to max mA. At 0 mA the extraction voltage is negative with respect to the emitters 58 (gridding). At max mA, the extractor voltage is positive. For intermediate mA the extractor voltage assumes intermediate values, that can be both positive and negative.

Figure 7:
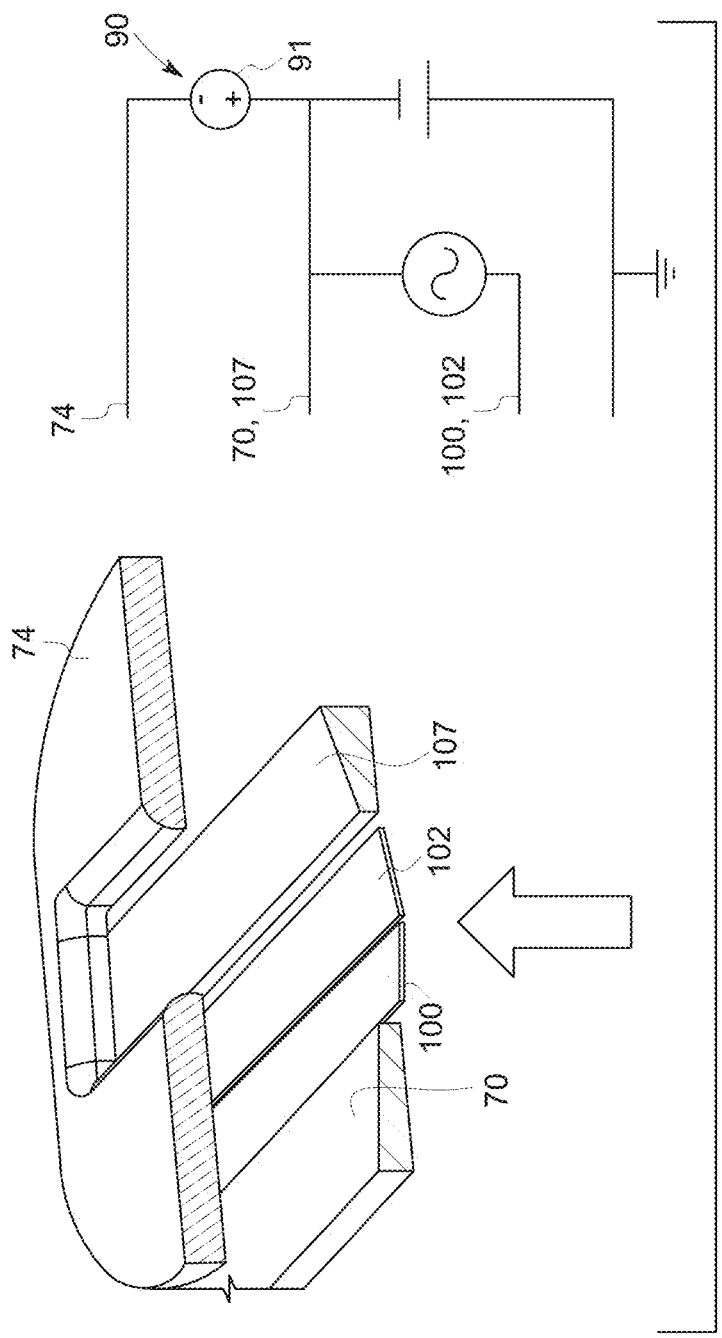
FIG. 7 is a cross-sectional view of the injector of FIG. 5.

More particularly, in another exemplary, non-limiting embodiment for operating the X-ray tube 52 illustrated in FIG. 7, via circuit 90 an AC current is applied to the emitters 58, 100,102 in order to create thermionic emission of electrons form the emitters 58,100,102 as a result of the Joule heating of the emitters 100,102. The voltage supplied by the current to the emitters 100,102 varies with time can oscillate between being greater and less than the tube voltage, such as on the order of ±20V. In this embodiment, the focusing electrode 70, 107 disposed around the emitters 100,102 can be maintained at the tube voltage. The focusing electrode 70 focuses the electron beam 64, while the extraction electrode 74 controls the intensity of the electron beam 64, as discussed previously. To do so, the extraction electrode 74 can be adjusted between a positive (extraction) or negative (gridding) bias voltage using extractor voltage tab 91 with respect to the emitters 100,102. The circuit 90 provides a tube or accelerating voltage between the cathode 52/emitters 100,102 and the anode 54, 56 in order to direct and accelerate the electron beam produced by the emitters 100,102 through the extraction electrode 74 and towards the anode or target 54,56. The voltage supplied to the extraction electrode 74 via the circuit 90 is varied to change the intensity of the electron beam 64 from the emitters 100,102. At a gridding voltage $V_{grid}$ supplied to the extraction electrode 74, the extraction electrode 74 functions to provide a repelling force on the electron beam from the emitters 100,102, thereby preventing passage of the electron beam through the extraction electrode 74, "gridding" the electron beam, and reducing the intensity of the electron beam to zero. The voltage $V_{grid}$ is determined by the accelerating voltage applied between the cathode 52 and the anode 56, with a higher acceleration voltage consequently requiring a more negative $V_{grid}$. By changing or increasing the voltage supplied to the extraction electrode 74 from $V_{grid}$, the intensity of the electron beam passing through the extraction electrode 74 can be adjusted, such as during an x-ray exposure, to place the extraction electrode 74 at a positive or negative bias relative to the emitters 100,102 in order to control the intensity of the electron beam in real-time.

Furthermore, voltage shifts of 20 kV or less may be applied to the extraction electrode 74 to control the intensity of the electron beam 64. In certain embodiments, these voltage shifts may be applied to the extraction electrode 74 via use of a control electronics module 92. The control electronics module 92 changes the voltage applied to the extraction electrode 74 in intervals of 1-15 microseconds to intervals of about at least 150 milliseconds. In one embodiment, the control electronics module 92 may include Si switching technology circuitry to change the voltage applied to the extraction electrode 74. In certain embodiments, where the voltage shifts range beyond 20 kV, a silicon carbide (SiC) switching technology may be applied. Accordingly, changes in voltage applied to the extraction electrode 74 facilitates changes in intensity of the electron beam 64 in intervals of 1-15 microseconds, for example. This technique of controlling the intensity of the electron beam in the order of microseconds may be referred to as microsecond intensity switching.

Additionally, the exemplary X-ray tube 50 may also include a magnetic assembly 80 for focusing and/or positioning and deflecting the electron beam 64 on the target 56. In one embodiment, the magnetic assembly 80 may be disposed between the injector 52 and the target 56, and in one exemplary embodiment at a distance of between 20-40 mm from the anode or extraction electrode 74. In one embodiment, the magnetic assembly 80 may include one or more multipole magnets for influencing focusing of the electron beam 64 by creating a magnetic field that shapes the electron beam 64 on the X-ray target 56. The one or more multipole magnets may include one or more quadrupole magnets, one or more dipole magnets, or combinations thereof. As the properties of the electron beam current and voltage change rapidly, the effect of space charge and electrostatic focusing in the injector will change accordingly. In order to maintain a stable focal spot size, or quickly modify focal spot size according to system requirements, the magnetic assembly 80 provides a magnetic field having a performance controllable from steady-state to a sub-30 microsecond time scale for a wide range of focal spot sizes. This provides protection of the X-ray source system, as well as achieving CT system performance requirements. Additionally, the magnetic assembly 80 may include one or more dipole magnets for deflection and positioning of the electron beam 64 at a desired location on the X-ray target 56. The electron beam 64 that has been focused and positioned impinges upon the target 56 to generate the X-rays 84. The X-rays 84 generated by collision of the electron beam 64 with the target 56 may be directed from the X-ray tube 50 through an opening in the tube casing 72, which may be generally referred to as an X-ray window 86, towards an object (not shown in FIG. 3).

With continuing reference to FIG. 3, the electrons in the electron beam 64 may get backscattered after striking the target 56. Therefore, the exemplary X-ray tube 50 may include an electron collector 82 for collecting electrons that are backscattered from the target 56. In accordance with aspects of the present technique, the electron collector 82 may be maintained at a ground potential. In an alternative embodiment, the electron collector 82 may be maintained at a potential that is substantially similar to the potential of the target 56. Further, in one embodiment, the electron collector 82 may be located adjacent to the target 56 to collect the electrons backscattered from the target 56. In another embodiment, the electron collector 82 may be located between the extraction electrode 74 and the target 56, close to the target 56. In addition, the electron collector 82 may be formed from a refractory material, such as, but not limited to, molybdenum. Furthermore, in one embodiment, the electron collector 82 may be formed from copper. In another embodiment, the electron collector 82 may be formed from a combination of a refractory metal and copper.

Furthermore, it may be noted that the exemplary X-ray tube 50 may also include a positive ion collector (not shown in FIG. 3) to attract positive ions that may be produced due to collision of electrons in the electron beam 64 with the target 56. The positive ion collector is generally placed along the electron beam path and prevents the positive ions from striking various components in the X-ray tube 50, thereby preventing damage to the components in the X-ray tube 50.

Referring now to FIGS. 4-9, 12-13 and 16, in the presently contemplated configuration, in the X-ray tube 50 having the electrostatic mA control described previously, the emitters 58 are formed as a pair of flat emitters 100,102 disposed within the injector/cathode assembly 52 at an angle with respect to one another. In the illustrated exemplary embodiment, the injector/cathode assembly 52 is mounted to a high voltage insulator 104 disposed on an extender 105 (FIG. 17), as is known, and the emitters 100,102 are spaced from one another without any intervening structure or septum disposed between the emitters 100,102, enabling the beams of electrons emitted from each emitter 100,102 to interact with one another as they project outwardly from the emitters 100,102.

The emitters 100,102 can be spaced from one another any suitable distance, but in the exemplary illustrated embodiment are spaced from about 50 μm to about 500 μm. However, in an alternative exemplary embodiment, the emitters 100,102 can be formed from a single sheet of material that is bent or otherwise deformed along a centerline of the material to form the emitters 100,102 on each half of the material. The material containing the emitters 100,102 can subsequently be attached, e.g., welded or brazed, to the injector 52. Further, in either embodiment above, the emitters 100,102 can be the same or different sizes, and/or can be the same or different shapes. In any configuration, the emitters 100,102 are positioned at an angle with regard to one another, as shown in FIGS. 5-8. While any suitable angle can be utilized for the emitters 100,102, in the exemplary illustrated embodiment the emitters 100,102 are positioned on the injector 52 at angles from a horizontal, as defined by plane H in FIG. 13, with the emitters 100,102 angled towards each other. In an exemplary embodiment, said angles range from about 1 degree to about 45 degrees or, in other exemplary embodiments, from about 2 degrees to about 20 degrees or, in other exemplary embodiments, from about 4 degrees to about 12 degrees. In other exemplary embodiments only one of the emitters is positioned at an angle within one of the above ranges from the defined horizontal, where the other emitter is parallel to said horizontal. It is further contemplated that both emitters 100,102 could be parallel to the defined horizontal, or at varying angles relative to said horizontal (i.e. both emitters can be positioned at the same angle relative to the defined horizontal, or the emitters can be positioned where one emitter is at one angle and the other emitter is at a different angle). Still further, the emitters 100,102 could be angled away from each other.

Figure 4:
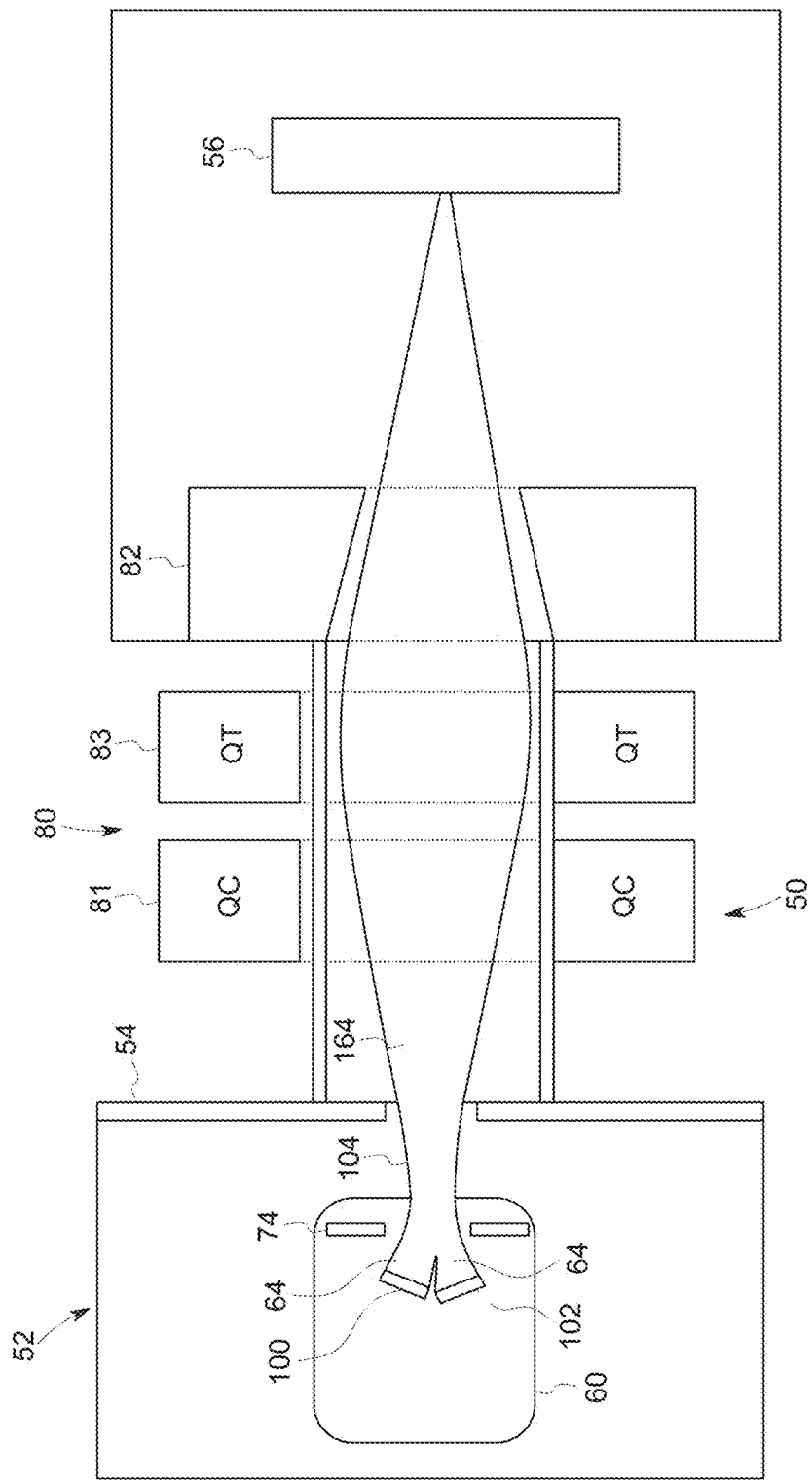
FIG. 4 is a schematic view of a CT system according to another exemplary embodiment of the invention.
Figure 5:
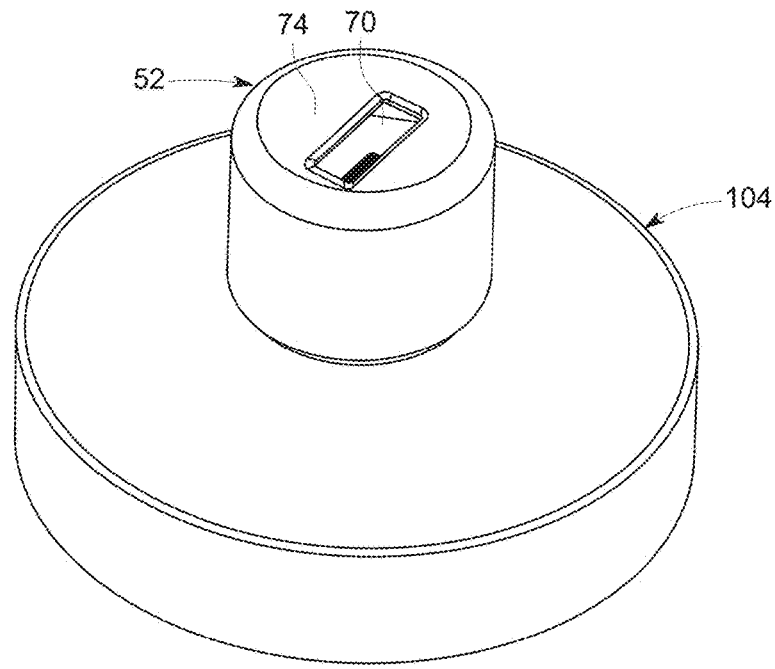
FIG. 5 is an isometric view of an injector/cathode assembly according to another exemplary embodiment of the invention.
Figure 6:
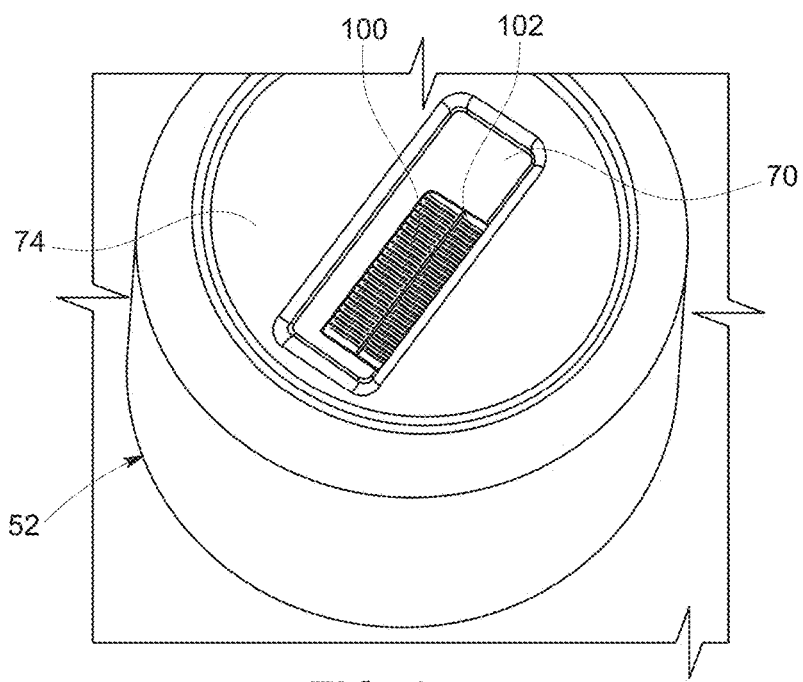
FIG. 6 is a partially broken away isometric view of the injector of FIG. 5.
Figure 12:
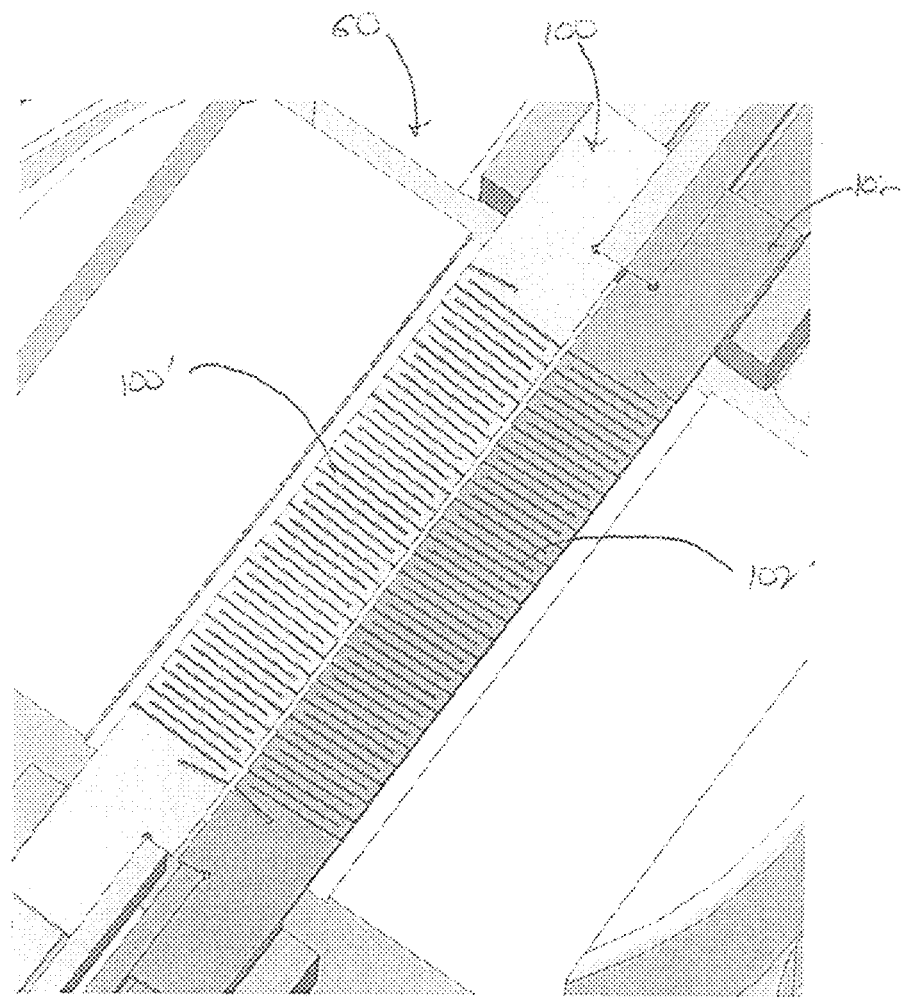
FIG. 12 is a partially broken away, isometric view of a pair of emitters within a cathode assembly according to another exemplary embodiment of the invention.
Figure 13:
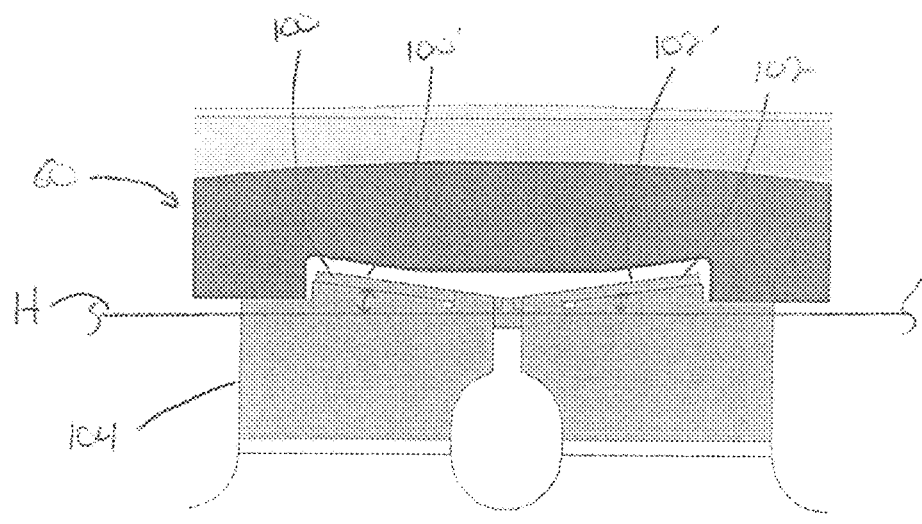
FIG. 13 is a partially broken away, cross-sectional view of the pair of emitters and cathode assembly of FIG. 12.
Figure 14A:
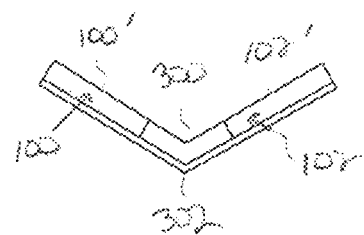
FIGS. 14A-14D are cross-sectional views of various constructions of pairs of emitters according to different exemplary embodiments of the invention.
Figure 14B:
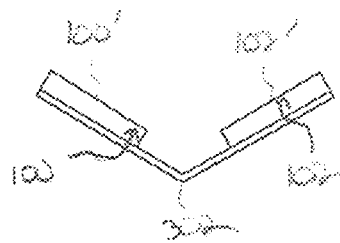
Figure 14C:
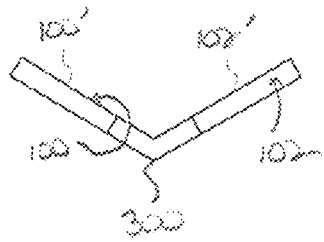
Figure 14D:
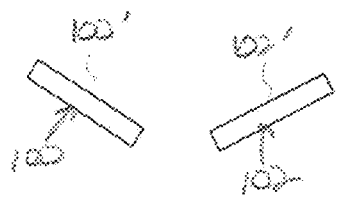

In the exemplary embodiments of FIGS. 4, 12 and 13, the emitters 100,102 are flat emitters, where the term "flat emitter" may be used to refer to an emitter that has a flat emission surface. In an alternative configuration the emitters 100,102 may be curved emitters or emitters including a curved portion thereon, such as in the width direction of the emitters 100,102. The curved emitter, which is typically concave in curvature along the long axis of each emitter 100,102, provides fine tuning or pre-focusing of the electron beam 64 from each emitter 100,102. As used herein, the term "curved emitter" may be used to refer to the emitter that has a curved emission surface. In accordance with aspects of the invention, shaped emitters 100,102 may also be employed. For example, in one exemplary embodiment, various polygonal shaped emitters 100,102 such as, a square emitter, or a rectangular emitter may be employed. However, other such shaped emitters 100,102 such as, but not limited to elliptical or circular emitters may also be employed. It may be noted that emitters 100,102 of different shapes or sizes may be employed based on the application requirements, including emitters 100,102 of different shapes or configurations.

In accordance with various exemplary aspects of the present technique, the emitters 100,102 may be formed from a low work-function material. More particularly, the emitters 100,102 may be formed from a material that has a high melting point and is capable of stable electron emission at high temperatures. The low work-function material may include materials such as, but not limited to, tungsten, thoriated tungsten, lanthanum hexaboride, and the like. Further, the emitters 100,102 can be formed in any desired manner of any desired material and configuration, such as that disclosed in co-pending and co-owned U.S. patent application Ser. No. 14/586,066, entitled Low Aberration, High Intensity Electron Beam For X-Ray Tube, the entirety of which is expressly incorporated herein by reference for all purposes.

The emitters 100,102 each include an emission surface 100',102' that form the angled portion of the emitters 100, 102 and that emits an electron beam 64 therefrom upon passage of a current through the emitters 100,102. In certain exemplary embodiments, the emitters 100,102 and emission surfaces 100',102' can be formed as disclosed in co-pending and co-owned U.S. Non-Provisional patent application Ser. No. 15/085,419, entitled Fabrication Methods And Modal Stiffening For Non-Flat Single/Multi-Piece Emitter, (the '419 application) the entirety of which is expressly incorporated herein by reference for all purposes. Emission surfaces 100,102 may be formed to be electrically isolated from one another or wired in either wired in series or parallel. As shown in FIGS. 14A-14D, in certain exemplary embodiment the emitters 100,102 and/or emission surfaces 100',102' can be formed completely separately from one another, or can be formed to be connected to one another using a ligament 300 that extends between the emitters 100,102 and/or emission surfaces 100',102', such as between one end of each of the emitters 100,102 and/or emission surfaces 100',102'. Further, in other exemplary embodiments, the emitters 100,102 and/or emission surfaces 100', 102' can be formed to be connected by a substrate 302 on which the emitters 100,102 and/or emission surfaces 100', 102' are placed, optionally in conjunction with a ligament 300 In still other exemplary embodiments, the shape of the current path along the emitters 100,102 and/or emission surfaces 100',102' can be formed as desired, such with a sinusoidal or switchback configuration, as shown in FIG. 13, or in any other suitable or desired configuration, such as those shown in the '419 application and/or in co-pending and co-owned U.S. Non-Provisional patent application Ser. No. 15/086,257, entitled Angled Flat Emitter For High Power Cathode With Electrostatic Emission Control, (the '257 application) the entirety of which is expressly incorporated herein by reference for all purposes.

Figure 15:
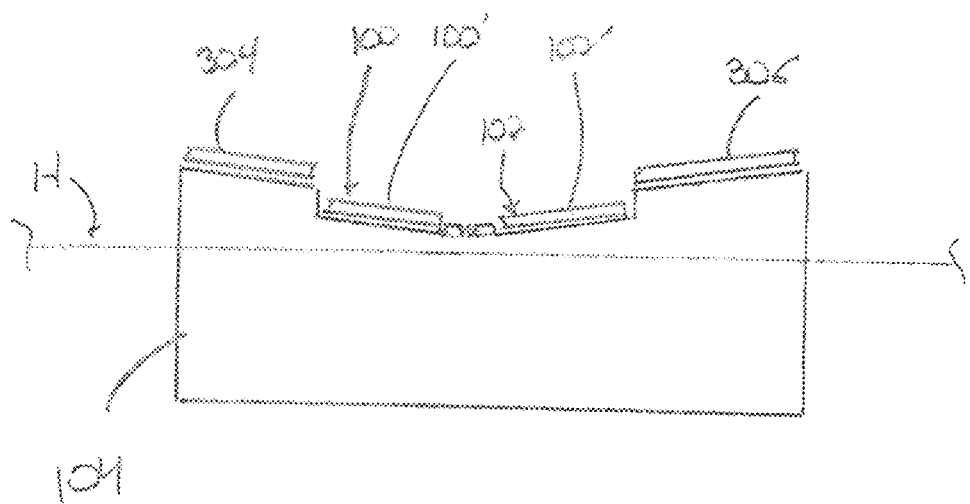
FIG. 15 is a cross-sectional view of a cathode assembly according to one exemplary embodiment of the invention.

Looking now at FIG. 15, the emitters 100,102 and/or emission surfaces 100',102' are positioned adjacent one another in the cathode assembly 60 in order to form a first pair of emitters 100,102. In other exemplary embodiments, the cathode assembly 60 can include an additional or second pair of emitters 304,306 disposed within the cathode assembly 60 at locations spaced outwardly from the emitters 100,102 and/or emission surfaces 100',102'. The second pair of emitters 304,306 can be formed similarly to the emitters 100,102, to operate similarly, and can be positioned at an angle relative to one another and to the horizontal plane H, such as at an angle within a range of 2 degrees to 20 degrees from horizontal, as defined by plane H. Additionally, the present invention contemplates that emitters 304 and 100, as well as emitters 305 and 102, respectively, may be coplanar or may be angled with respect to each other.

Figure 8:
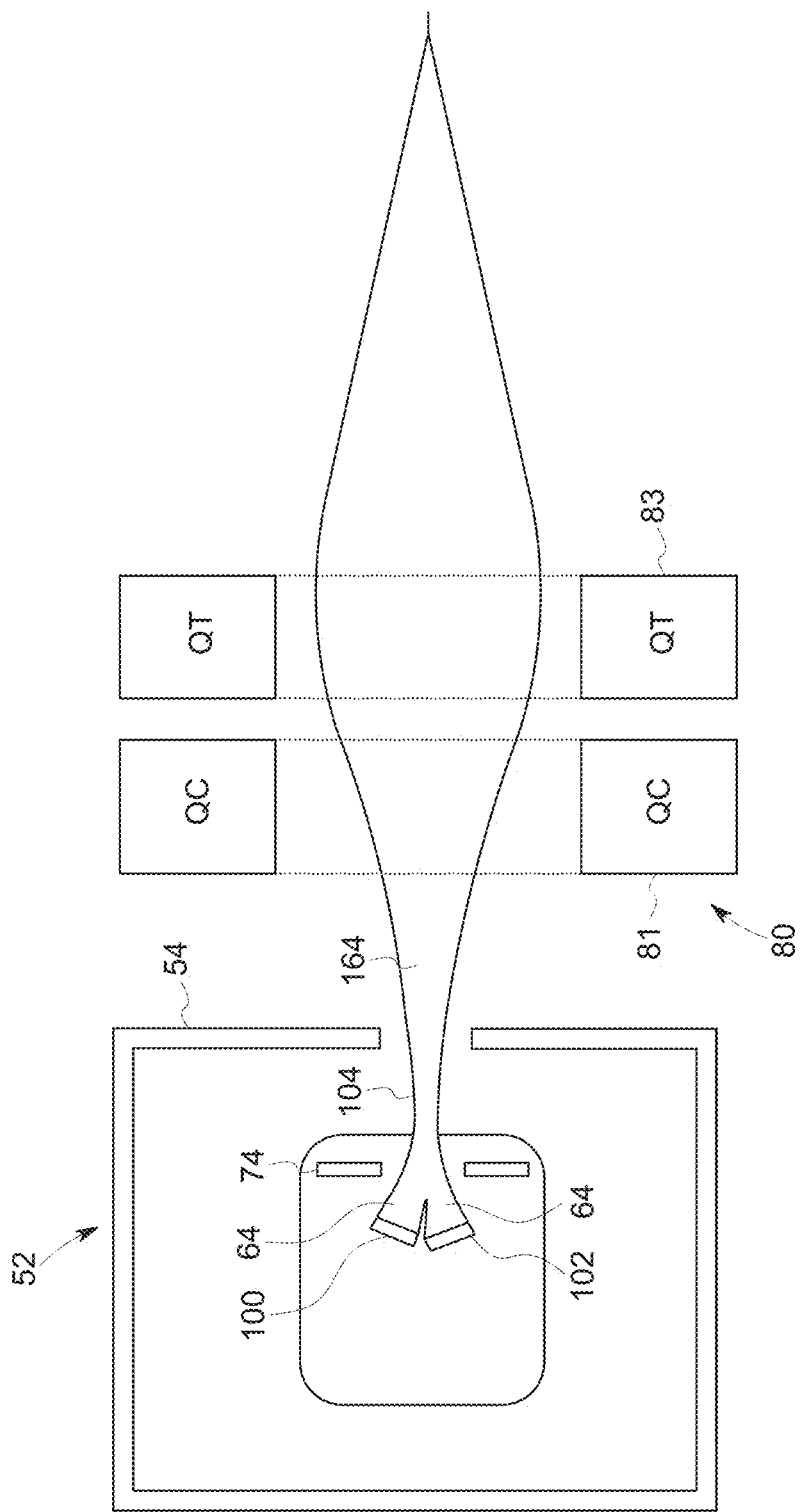
FIG. 8 is a schematic view of a low emission current application of an X-ray tube according to another exemplary aspect of the invention.
Figure 9:
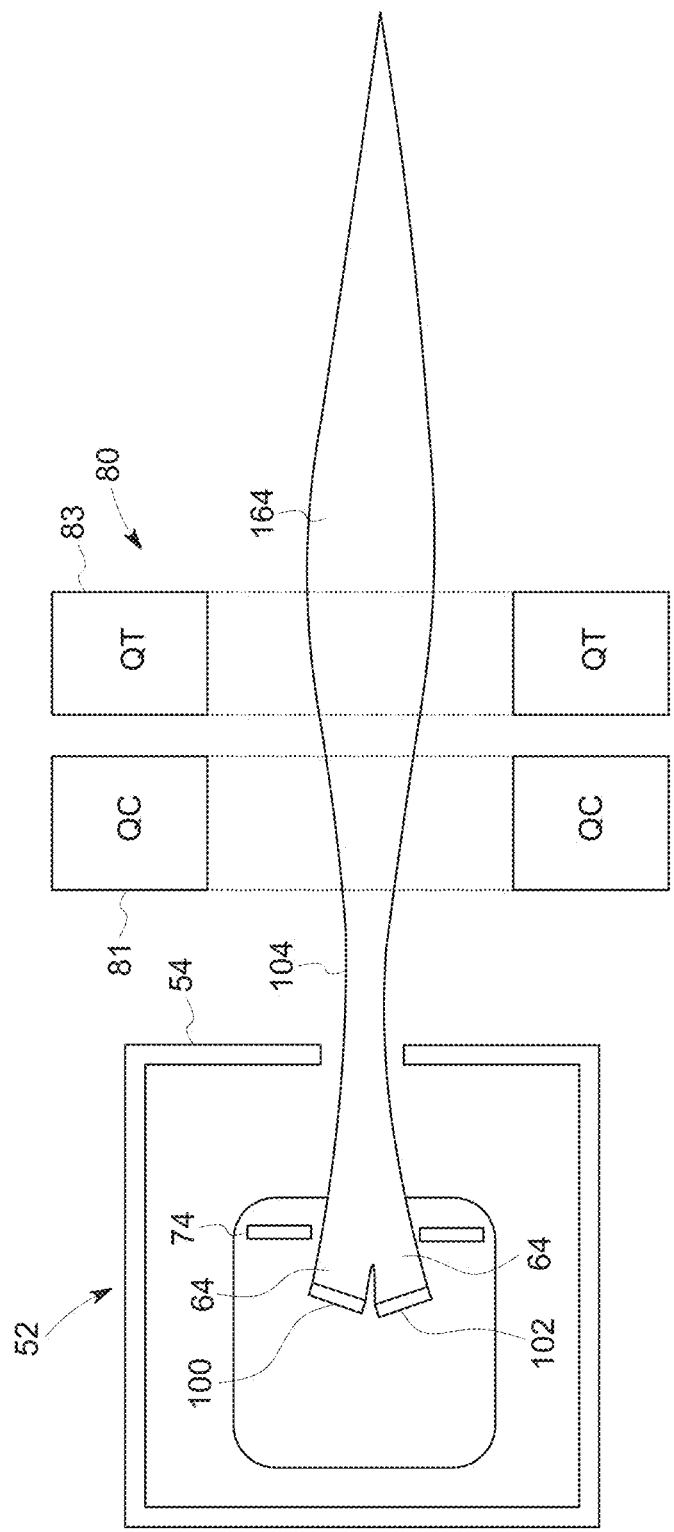
FIG. 9 is a schematic view of a high emission current application of an X-ray tube according to another exemplary aspect of the invention.

Referring now to the exemplary embodiment of FIGS. 4 and 8-9, upon simultaneous emission from the emission surfaces 100',102' of the emitters 100,102, the electron beams 64 combine into a single beam 164. In FIG. 8, in the case of a low emission current, which in an exemplary embodiment can be less than 0.28 mA/kV^1.5 or about 200 mA at 80 kV applied to the emitters 100,102, the combined beam 164 converges at a point or waist 104 close to the cathode or focusing electrode 70 due to a low amount of space charge in the beam 164, i.e. internal repulsion in the beam 164 due to the interaction or repellence of the electrons in the beam 164. Thus, when the beam 164 reaches the magnetic focusing assembly 80, which in the exemplary embodiment is formed of defocusing quadrupole magnet 81 and focusing quadrupole magnet 83, the beam 164 is expanding and can easily be focused onto the target 56 by the magnets 81,83.

In FIG. 9, when the emission current applied to the emitters 100,102 is high, e.g., an emission current up to between 1-2 A, due to the added space charge of the electron beam 164 as a result of the increased emission current, the beam waist 104 is moved more downstream away from the cathode or focusing electrode 70. However, due to the angled geometry of the emitters 100,102, a larger total surface area of the emitters 100,102 can be realized that leads to reduced space charge. The use of a curved emitter surface may be better, but there do not currently exist manufacturing methods to produce a curved surface, directly heated emitter. Alternatively, indirectly heated curved surface emitters are a possibility, but at a significantly higher cost to the cathode and increased cathode control complexity. Two angled flat surfaces for the emitters 100,102 turn out to be a great approximation to a curved surface, leveraging the benefits of curvature for focusing and direct heating for manufacturability. This in turn creates a greater initial convergence of the beams 64 into combined beam 164, overcoming the repulsion forces of the individual electrons in the beam 164, which leads to reduced space charge, and the positioning of the beam waist 104 upstream of the magnetic assembly 80. Thus, when the beam 164 enters the quadrupole focusing volume/magnetic assembly 80, the electron beam 164 is expanding and can be easily focused by the magnets 81,83 even at the very high emission currents between 0.5 A-2 A or 1-2 A at tube voltages below 80 kV or even below 70 kV.

Figure 10:
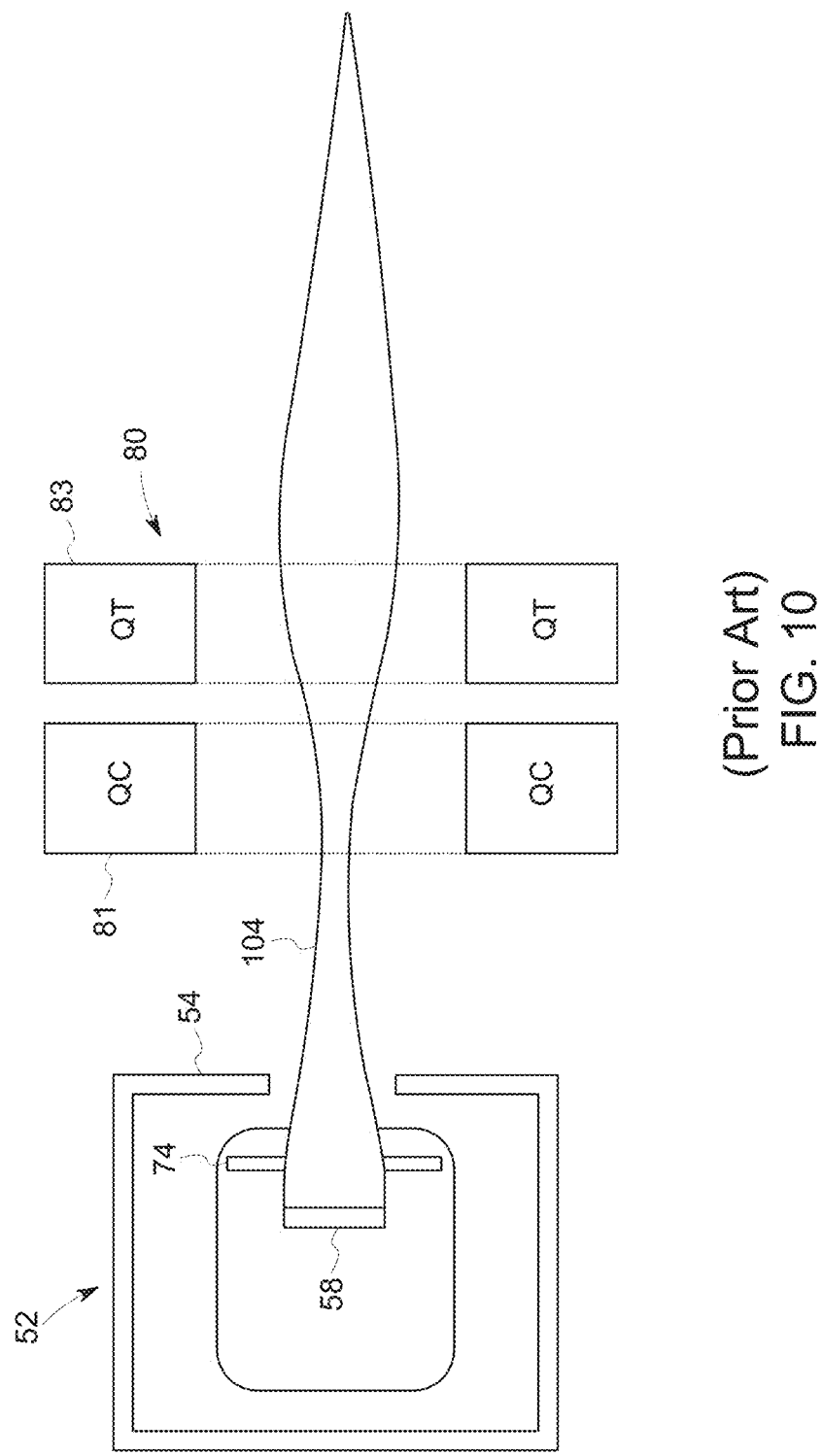
FIG. 10 is a schematic view of a high emission current application of a prior art X-ray tube.

In contrast, referring to FIG. 10, in the prior art high emission current situation where a flat emitter 58 is utilized that is not angled, due to the non-angled emitter geometry the electron beam 64 launches in an orientation closer to a parallel beam. Furthermore, with the consequent added space charge of the electron beam 64, the beam waist 104 is moved more downstream from the cathode/focusing electrode 70. When the emission current is high enough, i.e., approximately between 0.6 A-0.7 A, the waist 104 is positioned within the magnet 81 of the assembly 80, rendering the magnet 81 very ineffective for focusing the beam 64 in the width plane without the use of excessively high magnet currents (e.g., 30-40 A) in the assembly 80, and well above the current limits for the magnets 81,83.

Figure 11A:
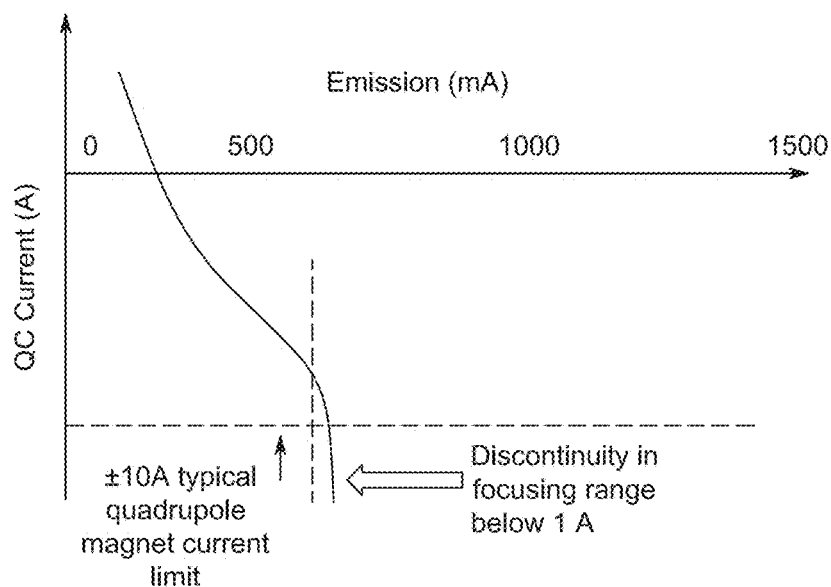
FIG. 11A-11B are graphs comparing the operating emission currents that can be utilized in the prior art X-ray tubes and in the X-ray tubes according to an exemplary embodiment of the invention.
Figure 11B:
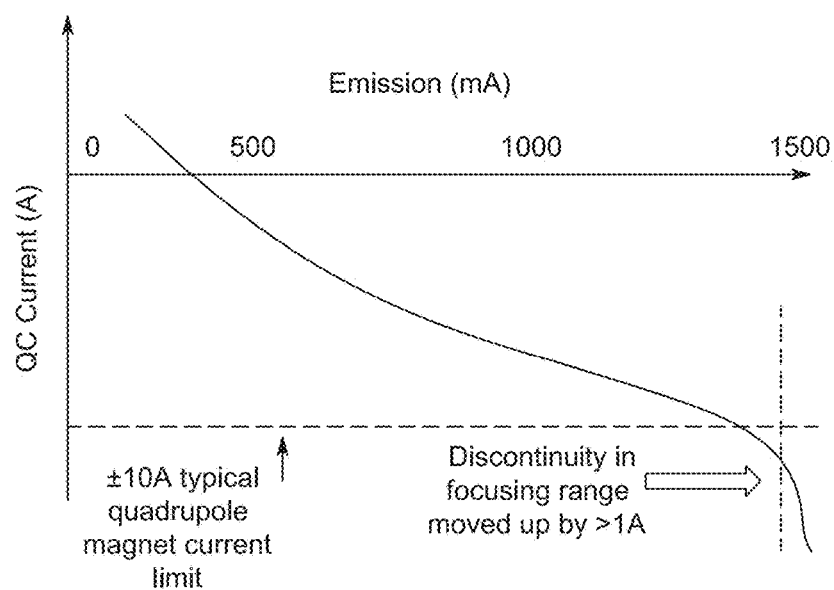

This result is graphically illustrated in FIG. 11A which shows that the use of high emission currents, such as above about 0.5 A, cause the discontinuity of the focusing range in an X-ray tube 50 including a non-angled emitter 58. In contrast, in FIG. 11B, the use of angled emitters 100,102 in an X-ray tube 50, such as those utilized in CT systems 10, shift the appearance of the discontinuity out to emission currents of approximately 1.5 A, increasing the emission currents that can be utilized to increase the emission of the tube 12 without consequent increases in the temperature required for the emission, as required in prior art X-ray tubes. As a result, the tube 50 will not degrade due to excessive heating thereby significantly extending the useful life of the tube 12 while maintaining focal spot size, and intensity and position of the electron beam 164 in the exemplary X-ray tube 50 resulting in improved image quality of the CT imaging system 10.

The written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:
1. An X-ray tube comprising:
a cathode assembly on which is disposed a pair of emission surfaces for generating a pair of electron beams, the pair of emission surfaces disposed at an angle with regard to one another;
a focusing electrode adjacent the cathode assembly for focusing the electron beams;
an extraction electrode spaced from the focusing electrode opposite the cathode assembly for controlling the intensity of the electron beam by adjusting a positive or negative voltage applied to the extraction electrode;

a magnetic assembly spaced from the extraction electrode opposite the focusing electrode; and a target spaced from the magnetic assembly opposite the extraction electrode.

2. The X-ray tube of claim 1 wherein the magnetic assembly comprises one or more multipole magnets.

3. The X-ray tube of claim 2, wherein the one or more multipole magnets comprise one or more quadrupole magnets, one or more dipole magnets, or combinations thereof.

4. A method for focusing an electron beam emitted from an X-ray tube, the method comprising the steps of:

providing an X-ray tube including a cathode assembly on which is disposed a pair of emission surfaces for generating a pair of electron beams, the pair of emission surfaces disposed at an angle with regard to one another, a focusing electrode adjacent the cathode assembly, an extraction electrode spaced from the focusing electrode opposite the cathode assembly that can be can be adjusted between a positive and negative bias relative to the pair of emission surfaces, a magnetic assembly spaced from the extraction electrode opposite the focusing electrode and a target spaced from the magnetic assembly opposite the extraction electrode capable of generating X-rays when impinged upon by the electron beams;

passing an emission current through at least one of the pair of emission surfaces to generate an electron beam; and passing a focusing current through the magnetic assembly to focus the electron beam onto the target.

5. The method of claim 4, further comprising the step of applying a positive or negative biasing voltage to the extraction electrode to control the intensity of the electron beam.

6. A computed tomography system comprising:

a gantry;

an X-ray tube coupled to the gantry, the X-ray tube comprising a cathode assembly having a pair of emission surfaces for generating an electron beam, the pair of emission surfaces disposed therein at angles with respect to one another, a focusing electrode for focusing the electron beam, and an extraction electrode which controls the intensity of the electron beam though the adjustment of a positive or negative biasing voltage applied to the extraction electrode; and a target for generating X-rays when impinged upon by the electron beam.

7. The computed tomography system of claim 6, further comprising a magnetic assembly located between the cathode assembly and the target for focusing the electron beam towards the target; an X-ray controller for providing power and timing signals to the X-ray tube; and one or more detector elements for detecting attenuated X-ray beam from an imaging object.

8. A cathode assembly comprising:

an emitter having a first emission surface configured to emit a first electron beam therefrom and a second emission surface disposed on the cathode assembly and configured to emit a second electron beam therefrom, wherein the first emission surface and the second emission surface are disposed at an angle with regard to one another; and an extraction electrode which controls the intensity of the electron beam though the adjustment of a positive or negative biasing voltage applied to the extraction electrode.

9. The cathode assembly of claim 8 wherein the first emission surface and the second emission surface are each disposed at an angle of between 1°-45° with regard to an emitter support.

10. The cathode assembly of claim 8 wherein the first emission surface and the second emission surface are electrically connected.

11. The cathode assembly of claim 10 wherein the first emission surface and the second emission surface are electrically connected approximate adjacent ends of the first emission surface and the second emission surface.

12. The cathode assembly of claim 11 wherein the first emission surface and the second emission surface are joined by a ligament extending between one end of each of the first emission surface and the second emission surface.

13. The cathode assembly of claim 8 wherein the first and second emission surface are electrically isolated.

14. The cathode assembly of claim 8 wherein the first emission surface is disposed on a first emitter and the second emission surface is disposed on a second emitter to form a first pair of emitters.

15. The cathode assembly of claim 14 further comprising a second pair of emitters disposed adjacent the first pair of emitters, the second pair of emitters disposed at angles with respect to one another and with respect to the first pair of emitters.

16. The cathode assembly of claim 8 wherein the first and second emission surfaces are substantially planar.

17. The cathode assembly of claim 8 wherein the first and second emission surfaces are curved, flat, partially curved, or any combination thereof.

18. The cathode assembly of claim 8 wherein the first and second emission surfaces are fitted to extend along portions of a continuous curved path.

19. The cathode assembly of claim 8 wherein the first and second emitters are formed of substantially uniform thickness.

20. The cathode assembly of claim 8 wherein the first and second emission surfaces are concave.

21. The cathode assembly of claim 8 further comprising a focusing electrode for focusing the electron beam.

22. A cathode assembly comprising an emitter having a first emission surface configured to emit a first electron beam therefrom and a second emission surface disposed on the cathode assembly and configured to emit a second electron beam therefrom, wherein the first emission surface and the second emission surface are disposed at an angle with regard to one another, wherein the first and second emission surfaces follow a sinusoidal pathway.

* * * * *